US006165486A

United States Patent [19]
Marra et al.

[11] Patent Number: 6,165,486
[45] Date of Patent: Dec. 26, 2000

[54] BIOCOMPATIBLE COMPOSITIONS AND METHODS OF USING SAME

[75] Inventors: Kacey G. Marra; Lee E. Weiss; Jay Wynn Calvert; Prashant N. Kumta, all of Pittsburg, Pa.

[73] Assignees: Carnegie Mellon University; University of Pittsburgh, both of Pittsburgh, Pa.

[21] Appl. No.: 09/196,288

[22] Filed: Nov. 19, 1998

[51] Int. Cl.[7] .............................. A61F 2/00; A61F 13/00
[52] U.S. Cl. ...................... 424/423; 424/422; 424/424; 424/425; 424/428
[58] Field of Search ............................. 424/423, 425; 606/230; 128/90

[56] References Cited

U.S. PATENT DOCUMENTS

| | | |
|---|---|---|
| 4,624,256 | 11/1986 | Messier et al. ................... 128/335.5 |
| 5,475,063 | 12/1995 | Kaplan et al. ........................ 525/411 |
| 5,522,895 | 6/1996 | Mikos ..................................... 623/16 |
| 5,679,723 | 10/1997 | Cooper et al. ........................ 523/115 |
| 5,766,618 | 6/1998 | Laurencin et al. ................... 424/426 |

*Primary Examiner*—Thurman K. Page
*Assistant Examiner*—Isis Ghali
*Attorney, Agent, or Firm*—Raymond A. Miller; Reed Smith Shaw & McClay LLP

[57] ABSTRACT

Blends of biodegradable polymers, preferably poly(caprolactone) and poly(D,L-lactic-co-glycolic) acid are discussed as well as their applications in the medical field, particularly with regard to bone tissue engineering. Preferably, hydroxyapatite ("HA") granules are incorporated into the blends and the resulting blends have desirable mechanical, physical, and biological characteristics. Even more preferably the compositions of the present invention are utilized to form osteoconductive composites that supported bone cell growth on the surface as well as throughout the scaffold.

16 Claims, 8 Drawing Sheets

(3 of 8 Drawing Sheet(s) Filed in Color)

BIOCOMPATIBLE COMPOSITIONS AND METHODS OF USING SAME

BACKGROUND OF THE INVENTION

1. Field of the Invention

The present invention relates to a biocompatible material which is useful as a tissue substitute and as a material for forming or coating biomedical devices.

2. Background and Description of the Related Art

Biocompatible materials and/or compositions have many uses in the medical field. Orthopedic surgeons, plastic surgeons and neurosurgeons, for example, frequently utilize substitute materials in their surgical procedures to augment or cement tissue. Bone substitution or augmentation, for example, is often required to repair or replace damaged, diseased, or congenitally absent tissue. The types of cases requiring bone augmentation range from and include trauma, congenital and degenerative diseases (i.e. spinal fusions), and cosmetic applications. Suitable materials for use as synthetic substitutes of muscular-skeletal tissue are preferably easy to apply, pliable, and shapeable, and are able to withstand the stresses, strains and compressive forces associated with the native tissue being replaced.

Biodegradable materials have been developed for use as implantable prostheses, as pastes, and as templates around which the body can regenerate various types of tissue. Polymers which are both biocompatible and resorbable in vivo are known in the art as alternatives to autogenic or allogenic substitutes. These resorbable biocompatible polymers include both natural and synthetic polymers. Natural polymers are typically absorbed by enzymatic degradation in the body, while synthetic resorbable polymers typically degrade by a hydrolytic mechanism. Synthetic resorbable polymers which are typically used to manufacture medical devices include homopolymers such as poly(glycolide), poly(lactide), poly($\epsilon$-caprolactone), poly(trimethylene carbonate) and poly(p-dioxanone) and copolymers such as poly(lactide-co-glycolide), poly($\epsilon$-caprolactone-co-glycolide), and poly(glycolide-co-trimethylene carbonate). The polymers may be statistically random copolymers, segmented copolymers, block copolymers, or graft copolymers or combinations of any of the above.

The substitutes or pastes preferably have properties which allow them to be contoured into the defect site and are biodegradable. It is also preferable that they are capable of sustaining the mechanical stresses in the respective environments in which the bone substitute are placed. It is also preferable that the materials are able to integrate into surrounding tissues and become substantially vascularized. Inability to accept vascular ingrowth may increase the risk for infection. If infected, the materials must be removed in order to avoid further systemic infection.

SUMMARY OF THE INVENTION

The present invention is directed to compositions useful as delivery systems, substitute tissue, and in the manufacture of biomedical articles. The term "tissue", unless expressly otherwise noted herein, refers to an aggregation of similarly specialized cells united in the performance of a particular function. As used herein, the term "tissue" specifically includes connective tissue (e.g., hard forms such as osseous tissue (bone)) as well as other muscular or skeletal tissue. Preferably, the compositions of the present invention are osteoconductive and/or osteoinductive.

In a preferred embodiment, the present invention is directed to a composition which is comprised of a biocompatible copolymer and a biocompatible polyester. When used as a bone substitute the composition preferably includes a bioceramic material. The biocompatible copolymer preferably is a copolymer of poly(lactic) acid and poly(glycolic) acid, the biocompatible polyester is preferably a polycaprolactone, and the bioceramic component is preferably exemplified by a coralline hydroxyapatite or sintered calcium hydroxyapatite. The bioceramic materials are intended to mimic a mineralized bone component. Hydroxyapatite ("HA") is the preferred bioceramic material because it renders the composition substantially osteoinductive and/or osteoconductive. Most preferably, the biodegradable composition is comprised of a blend of copolymer, polyester and bioceramic material. As used herein, a "blend" refers to a physical mix of polymers (e.g., a physical mix of copolymer, polyester, and bioceramic with little or no covalent bonding between the respective constituents. It is preferable that the concentration of the polyester be less than about 50% with respect to the copolymer, even more preferably less than about 40% with respect to the copolymer, and most preferably the polyester is at a concentration of about 10% with respect to the copolymer.

An alternate embodiment of the present invention is a composition comprised of a copolymer of poly(lactic) acid and poly(glycolic) acid and polycaprolactone wherein the copolymer and the polycaprolactone are blended at a predetermined ratio to provide a desirable characteristic. It is preferable that the predetermined ratio be in the range of about 10:90 polyester to copolymer to about 50:50 polyester to copolymer. If the tissue is to replace, augment or serve as a substitute for hard tissue such as bone, the composition preferably includes bioceramic material such as hypoxyapatite in the range of about 0–25 weight % hydroxyapatite to total polymer (copolymer and polyester) more preferably in the range of about 1% to about 20%, even more preferably, about 5% to about 15% HA, and most preferably about 10% HA. Although the range of 10:90 polyester to copolymer to 50:50 polyester to copolymer is acceptable, it is preferable that the composition include more copolymer than polyester.

Some of the uses of the composition which include the hydroxyapatite are: a bone substitute; paste; or cement. The present invention is particularly useful in treating patients having a major bone defect (e.g., cranio-facial). If the tissue being replaced, augmented, or substituted or the device being formed does not benefit from incorporation of a mineralized component, it is advisable to substantially omit hydroxyapatite from the blend. This is because incorporation of hydroxyapatite results in a more "brittle" device. Minimal or no hydroxyapatite is desirable where a brittle characteristic renders the device or article less useful e.g., sutures, anchors, fixation systems such as sutures, suture anchors, staples, surgical tacks, clips, plates and screws. It is also advisable to avoid large concentrations (i.e., above 10% by weight) of hydroxyapatite soft tissue applications such as tissue used to substitute or augment breast tissue.

Another embodiment of the present invention is a prosthetic template comprised of a biodegradable polymer, a bioceramic material, and a biodegradable polyester wherein the biodegradable polyester and the biodegradable polymer are chemically distinct. In this embodiment it is preferable that the biodegradable polymer be a copolymer of poly(lactic) acid and poly(glycolic acid), the polyester be polycaprolactone, and the bioceramic be hydroxyapatite. As above, it is preferable that the biodegradable polymer and the biodegradable polyester be blended at a predetermined ratio (i.e., about 10:90 to 50:50 biodegradeable polyester to biodegradable polymer).

Another embodiment of the present invention is a composition which is comprised of biocompatible copolymer, bioceramic material and biocompatible polyester. This embodiment has the preferred ranges of copolymer, bioceramic and polyester as described above and is most preferably a blend of poly(lactic-co-glycolic) acid, polycaprolactone, and hydroxyapatite. Uses for the composition include bone augmentation, bone prosthesis, bone cement, hard tissue implant, and bone scaffolding, fixation systems (e.g., screws, sutures, suture anchors, staples, surgical tacks, clips, plates and screws) and medical devices. The biodegradable implant of the present invention can be formed by a method which includes mixing the copolymer and the polyester together as a blend and then molding or shaping the blend to satisfy the implant needs of a patient. Depending on the intended use, appropriate amounts of the bioceramic is also blended with the copolymer and the polyester. It is preferable that the copolymer be poly(lactic-co-glycolic) acid, the bioceramic be hydroxyapatite, and the polyester be polycaprolactone. In this embodiment, it is preferably that the polycaprolactone is at a concentration of about 5–15%, more preferably about 8% to about 12% and more preferably about 10% by weight with respect to the copolymer.

An additional embodiment of the present invention is a delivery system for bioactive agents such as pharmaceuticals and/or cells. The drug delivery system preferably includes along with a biodegradable copolymer and polyester at a predetermined ratio as described above, a therapeutically effective amount of a bioactive agent such as a pharmaceutical agent or cell.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

The features, aspects and advantages of the present invention will become better understood with regard to the following description, appended claims, and accompanying drawings where:

DETAILED DESCRIPTION OF THE PRESENT INVENTION

Figure 1:
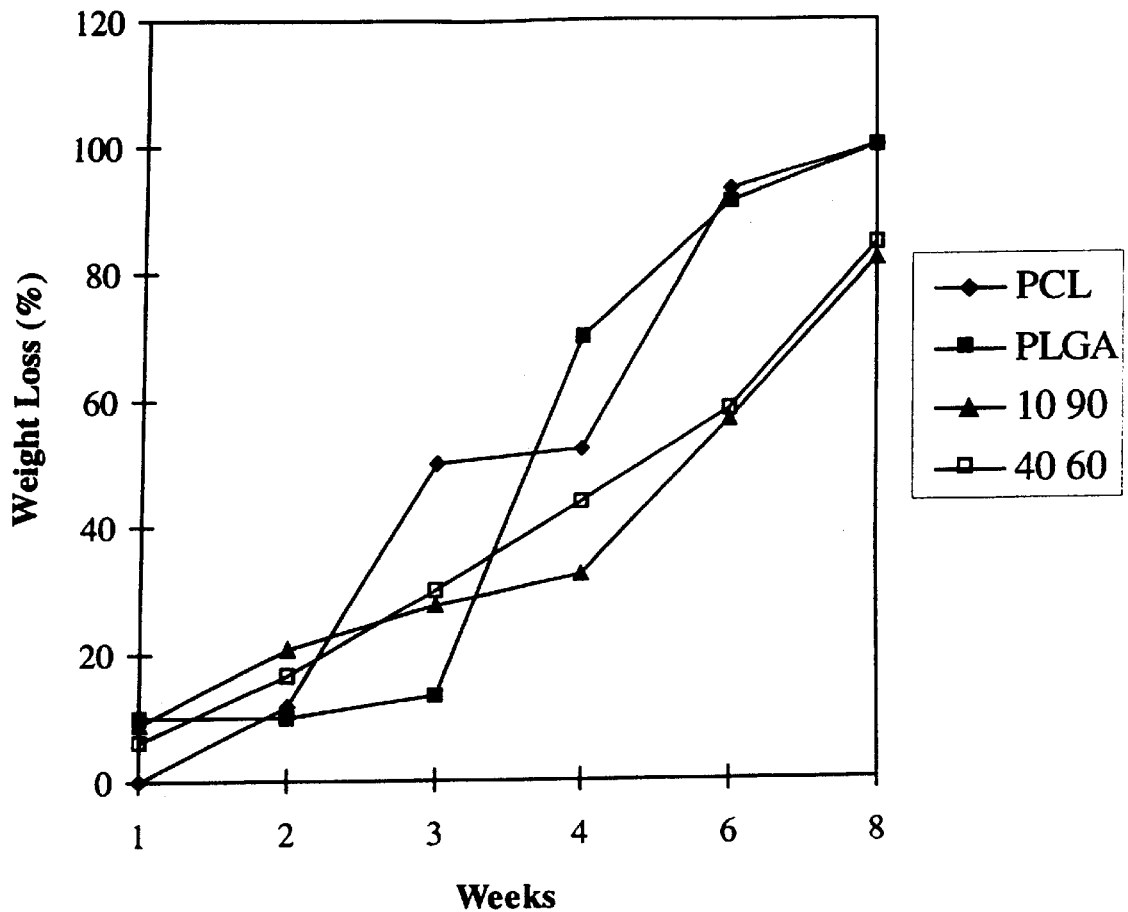
FIG. 1 illustrates in vitro degradation of polymer scaffolds constructed of predetermined ratio of copolymer (PLGA) to polyester (PCL)

The present invention is directed to biodegradable compositions. The composition may be used as a substitute for tissue or as a material for forming or coating biomedical devices. The composition may also be used as a vehicle for delivery of a therapeutic agent. The present invention is desirable because it exhibits a beneficial response such as supporting cell proliferation, supporting phenotypic differentiation, supporting vascularization, minor initial inflammatory response allowing for better cell survival, is biocompatible, and is resorbable.

Compositions of the present invention are preferably comprised of a blend of polymers such as poly(lactic-co-glycolic) acid (hereinafter "PLGA") and polyesters. For many of the intended applications it is preferable that the composition include a material which substantially mimics a mineralized bone component such as hydroxyapatite (hereinafter "HA").

The poly(lactide-co-glycolide) copolymers of the present invention preferably contain sufficient amounts of glycolide repeating units to effectively provide faster bio-absorption while providing the desired mechanical profile. The poly (lactide-co-glycolide) copolymers will typically contain about 25 mole percent to about 99 mole percent of lactide repeating units, and more preferably about 50 mole percent to about 95 mole percent of lactide repeating units. The copolymer of poly(lactic acid) (PLA), and poly(glycolic acid) (PGA), may be referred to herein as "PLGA". Biodegradable polyarylates may also be suitable copolymers in the present invention.

Aliphatic polyesters useful in the practice of the present invention are typically synthesized by conventional techniques using conventional processes. For example, in a ring opening polymerization, lactone monomers are polymerized in the presence of an organometallic catalyst and an initiator at elevated temperatures. The organometallic catalyst is preferably tin based, e.g., stannous octoate, and is present in the monomer mixture at a molar ratio of monomer to catalyst ranging from about 10,000/1 to about 100,000/1. The initiator is typically an alkanol, a glycol, a hydroxyacid, or an amine, and is present in the lactone monomer mixture at a molar ratio of monomer to initiator ranging from about 100/1 to about 5,000/1. The polymerization is typically carried out at a temperature range from about 80° C. to about 220° C., preferably from about 160° C. to about 200° C., until the desired molecular weight and viscosity are achieved. Under these conditions, the aliphatic polyesters, will typically have an average molecular weight of about 5,000 grams per mole to about 200,000 grams per mole, and more preferably about 10,000 grams per mole to about 100,000 grams per mole.

Suitable lactone monomers include p-dioxanone, trimethylene carbonate, ε-caprolactone, delta-valerolactone, beta-butyrolactone, ε-decalactone, 2,5-diketomorpholine, pivalolactone, α, α-diethylpropiolactone, ethylene carbonate, ethylene oxalate, 3-methyl-1,4-dioxane-2,5- dione, 3,3-diethyl-1,4-dioxan-2,5-dione, gamma-butyrolactone, 1,4-dioxepan-2-one, 1,5-dioxepan-2-one, 1,4-dioxan-2-one, 6,8-dioxabicycloctane-7-one and combinations of two or more thereof. The preferred lactone monomers are p-dioxanone, trimethylene carbonate and ε-caprolactone, with ε-caprolactone being empiracally preferred.

Although hydroxyapatite is the preferred bioceramic material used in the present invention, other calcium containing compounds such as mono-, di-, octa-, α-tri-, β-tri-, or tetra-calcium phosphate, fluoroapatite, calcium sulfate, calcium fluoride and mixtures thereof may also be used. Compositions of the present invention may also contain a bioactive glass comprising metal oxides such as calcium oxide, silicon dioxide, sodium oxide, phosphorus pentoxide, and mixtures thereof, and the like. It is preferable that the particle size of the hydroxyapatite be about 0.1 micron to about 500 microns, more preferably about 1 micron to about 250 micron, and even more preferably about 10 microns to about 100 microns.

The composition of the present invention is manufactured in a conventional manner. For example, the copolymer, polyester (i.e., homopolymer), and bioceramic material may be individually charged into a conventional mixing vessel having a conventional mixing device mounted therein such as an impeller or equivalents thereof (e.g., stirrer). The polymers and copolymers are then mixed at a temperature of about 150° C. to about 220° C., more preferably from about 160° C. to about 200° C., for about 5 to about 90 minutes, more preferably for about 10 to about 45 minutes or until a uniformly dispersed polymer blend is obtained. The polymer blend is further processed by removing it from the mixing device, cooling to room temperature, grinding, and drying under pressures below atmospheric at elevated temperatures for a period of time using conventional apparatuses and processes.

As used herein, the term "tissue" is intended to encompass all types of biological tissue including both hard and soft tissue. As used herein, the term "bone cement" is defined to mean a material which adheres to tissue such as cartilage and bone in order to fixate fractures and other bony defects as well as fixate fracture fixation devices in cartilage and bone, and to act as a scaffold for bone formation at the cement site. A bone cement should have good adhesive strength and provide a mechanism for bone ingrowth.

As used herein, the term "tissue substitute" is defined to mean a material which replaces tissue permanently or replaces tissue for a period of time until it is resorbed and replaced by the patient's own tissue. A tissue substitute should be similar in physical and biological properties to the patient's own tissue. The term "bone substitute" specifically refers to a replacement material of osseous tissue which is permanent or replaced with native bone tissue over time.

The specific materials and methods which were used in the devices, composition and methods exemplary of the present invention are as follows: poly(caprolactone)—"PCL", [Aldrich (Aldrich Mw 65 kDa)], poly(D,L-lactic acid-co-glycolic acid)—"PLGA" [Mw 40 kDa–65 kDa, (65:35)], "HA" hydroxyapatite [$Ca_{10}(PO_4)_6(OH)_2$, Aldrich], and $CHCl_3$ [Fisher]. These materials were utilized as received. PBS [phosphate-buffered saline] tablets were purchased from Sigma. NaCl [Aldrich] was sieved into particles of a diameter of 150–250 microns using ASTM-standard brass sieves (Fisher). Teflon beakers, brass sieves and pre-cleaned microscope slides were purchased from Fisher.

Polymer scaffolds were prepared using three different approaches: casting, cold-pressing, and hot-pressing techniques. Discs with porosity in the range of 40–90% and controlled thickness of from 0.6 to 40 mm were prepared. Blends of PCL and PLGA, with and without HA, were compared with the homopolymers. The polymers were dissolved in chloroform ($CHCl_3$) at room temperature (7–10% w/v) for particulate leaching. Sieved NaCl (150–250 μm particle size), and hydroxyapatite (~10 μm particle size), were suspended in the solution and sonicated for 60 seconds. After evaporation of the chloroform solvent, the scaffold was weighed and immersed in distilled water. After 24 hours at room temperature, the scaffold was removed from the water and dried. The weight of the scaffold was recorded. Polymer scaffolds (3–6 mm thick) that had been prepared using the solvent-casting technique, prior to leaching the NaCl, were cut into discs of a diameter of 12 mm. The discs were pressed at a pressure of 6,000–10,000 PSI using a Carver hydraulic press, Model 100. The amount of pressure applied controlled the thickness of the discs. The 1 mm thick discs were immersed in distilled water to dissolve the NaCl.

The general procedure for preparing blends using the cold-pressing technique involves taking polymer scaffolds that have been prepared using the solvent-casting technique, prior to leaching the NaCl, cutting them into discs of a diameter of 1.2 cm, and pressing at a pressure of 10,000 psi using a Carver hydraulic press. The 1 mm thick discs are then immersed in distilled water to dissolve the NaCl. The general procedure for preparing blends using the hot-pressing technique involves placement of cold-pressed polymer scaffolds in an oven at 130° C. for 15 minutes. The hot die containing the cold-pressed scaffold is pressed again at 10,000 psi using a Carver hydraulic press, cooled to room temperature, removed, and immersed in distilled water to dissolve the NaCl. Homopolymer discs as well as blends of 10/90 and 40/60 were prepared (10% PCL and 90% PLGA; 40% PCL and 60% PLGA, respectively).

Figure 2:
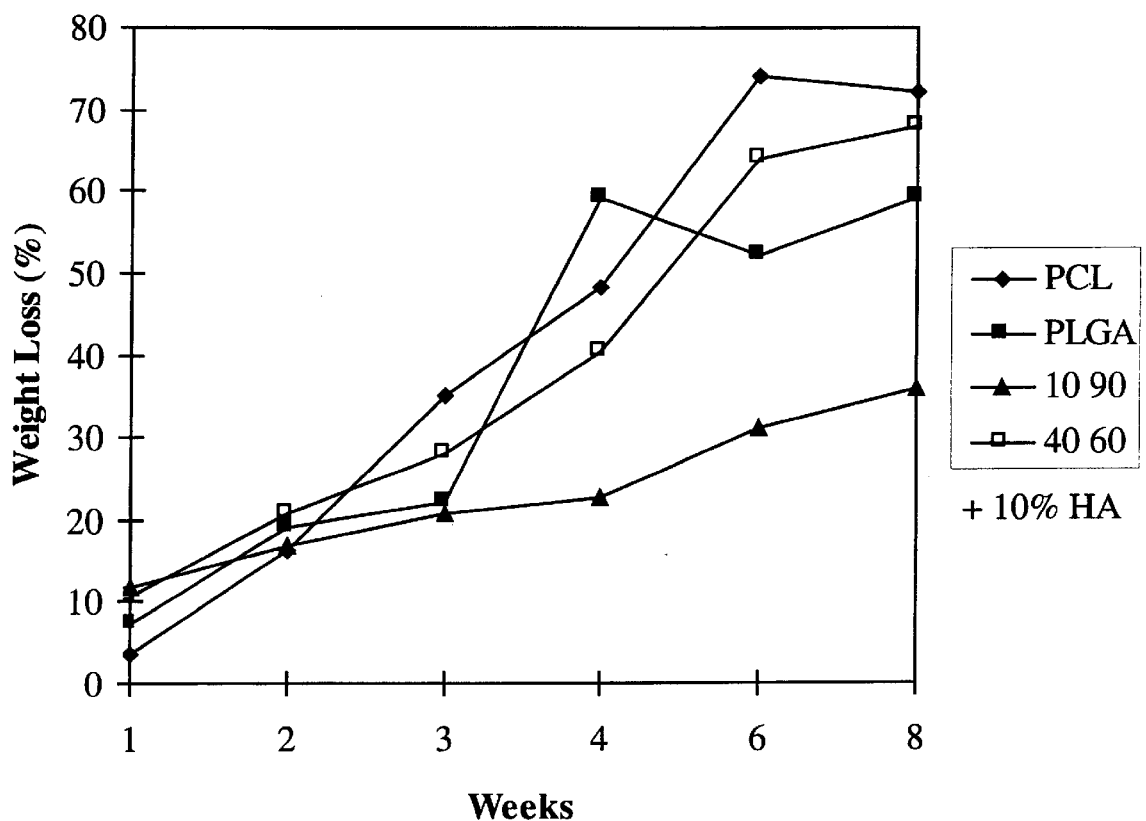
FIG. 2 illustrates in vitro degradation of polymer scaffolds constructed of predetermined ratio of copolymer (PLGA) to polyester (PCL) with 10% hydroxyapatite (HA) added to the blend.

As shown in FIGS. 1 and 2, weight loss during storage at 37° C. in phosphate-buffered saline (pH 7.4) was determined for the scaffolds. The porous scaffolds were 1 mm thick with a diameter of 7 mm. The buffer solution was changed every 2 weeks. The scaffold was removed, rinsed with distilled water, and air-dried at room temperature for 24 hours for measurement of weight loss at 1, 2, 3, 4, 6, and 8 weeks. The results were an average of three measurements.

The weight loss of the composites over an 8 week period was determined by gravimetric analysis. FIG. 1 displays the weight loss of the homopolymers and the blends; PCL; PLGA; 10% PCL/90% PLGA (10/90) and 40% PCL/60% PLGA (40/60), during an eight week period. From FIG. 1 and FIG. 2, it can be seen that the blends degrade at a slower rate than the homopolymers. As can be seen in FIG. 1, combining PCL and PLGA (65:35) results in slower degradation time. FIG. 2 illustrates the benefits of adding 10% HA. The 10:90 ratio of PCL:PLGA has a better degradation time with 10% HA added to the blend as opposed to the 40:60 (PCL:PLGA) with 10% HA. Since slower degradation is desirable for bone cement or bone substitution this is the most preferred composition for these applications.

The degradation rates of the blends containing 0–50% HA was also determined. The incorporation of 10% HA resulted in the most preferred degradation profile. Blends containing 50% HA were visibly chalky; HA granules appeared to leach out of the scaffolds during degradation. FIG. 2 displays the weight loss of the homopolymers and blends incorporated with is 10% HA. The 10:90 blend with 10% HA displayed the slowest degradation rate. Strips were cut from sheets of polymer composition samples were cut into strips of 12 mm length, 1 mm thickness and 6 mm width. Porosity was 80%

(as controlled by the amount of NaCl tensile strength and Young's modulus were determined with an Instron, Model 5500-R using Merlin Software at a crosshead speed of 2 mm/min. The load cell was an Instron static load cell (100 N). Results were an average of at least five measurements sites formed respectively of PCL, PLGA, 10:90 PCL/PLGA and 10:90 PCL/PLGA with 10% HA added. Samples were cut into strips of 12 mm length, 1 mm thickness and 6 mm width. Tensile strength and Young's modulus were determined with an Instron, Model 5500-R using Merlin Software at a crosshead speed of 2 mm/min. The load cell was an Instron static load cell (100 N). Results were an average of at least five measurements. For Table 1 below, samples were cut into strips of 12 mm length, 1 mm thickness and 6 mm width. Tensile strength and Young's modulus were determined with an Instron, Model 5500-R using Merlin Software at a crosshead speed of 2 mm/min. The load cell was an Instron static load cell (100 N). Results were an average of at least five measurements.

TABLE 1

Mechanical Properties of Scaffolds

|  | Tensile Strength (MPa) | Young's Modulus (MPa) |
| --- | --- | --- |
| Trabecular Bone | 1.2 | 50–100 |
| PCL | 1.1 ± 0.1 | 11.8 ± 4.0 |
| PLGA | 0.45 ± 0.08 | 2.4 ± 0.7 |
| 10/90 | 0.40 ± 0.1 | 2.5 ± 0.7 |
| 10/90 + 10% HA | 0.55 ± 0.09 | 12.3 ± 2.0 |

As shown by the Table 1 data, the addition of PCL to PLGA increases both the modulus and tensile strength compared to PLGA alone. Mechanical testing was carried out on the composites before and after degradation using an Instron. Using the Instron, both tensile strength and Young's modulus were determined. Typically, for cortical bone, the tensile strength is 124–140 MPa; for trabecular bone, the tensile strength value is 1.2 Mpa and for cortical and trabecular bone, the modulus values are 17–20 GPa and 50–100 MPa, respectively.

For the in vitro fresh bone marrow testing, nine six-month old, male New Zealand White Rabbits (Orycytolagus cuniculis) were purchased from a rabbit supplier (Myrtle's Rabbitry, Inc., Thompson Station, Tenn. 37179). All rabbits were housed individually and has ad-libitum access to Purina Rabbit Chow and water.

Bone marrow stromal cells were isolated from the femurs of New Zealand White rabbits. All animals were anesthetized with an intramuscular injection (0.59 mL/kg) of a solution of 91% ketamine hydrochloride (Ketaject, 100 mg/mL, Aveco, Fort Dodge, Iowa) and 9% xylazine (Xylaject, 20 mg/mL, Mobay Corp, Shawnee, Kans.). The rabbit was positioned in the supine position and the lower abdominal wall, inguinal region, and lateral surfaces of both thighs and legs were shaved, depilated, and prepared for aseptic surgery. A 4 cm long skin incision was made on the anterior aspect of the patella, and the quadriceps femoris muscle were displaced laterally. A drill and cutting burr was used to create a small femoral and tibial defect and a Fogarty balloon catheter was used to harvest bone marrow from the medullary canal. The bone marrow plugs were harvested by inflating the balloon and withdrawing it from the canal.

The bone marrow plugs were then mixed with 4 mL of heparinized IMDM tissue culture medium (GIBCO Laboratories, NY) in a test tube. The marrow was disaggregated by passing it gently through an 18 gauge IV catheter and syringe to create a single cell suspension. The suspension was centrifuged (250 g, 10 minutes) and some of the supernatant was discarded to concentrate the cell number. Two milliliters of venous blood was taken from the femoral vein through a small incision and autogenous serum was obtained by centrifugation. After adding autogenous serum (10% of total volume), the viability of the cells was >90% as checked by the tryptan blue dye exclusion method.

Cells were maintained in 75 cm$^2$ flasks in complete medium consisting of DMEM (Gibco), 15% fetal calf serum (FCS, Gibco), gentamin sulfate (25 µg/mL, Sigma), L-ascorbic acid (50 µg/mL, Sigma), sodium beta-glycerophosphate (10 mM, Sigma), penicillin G (50 µg/mL, Gibco), and dexamethasone (10 nM, Sigma). Cells were passaged every 2–3 days. After 10–14 days, cells had grown to confluency. Discs of polymeric blends with hydroxyapatite were sterilized by soaking in two changes of ethanol for 30 minutes, then soaking in four changes of PBS solution for 2 hours. The discs were immersed in individual 15 mm-diameter petri dishes filled with 1 mL of complete medium. Cells at a density of 40,000 cells/mL were added to each petri dish. Discs were incubated at 37° C. in a 5% $CO_2$ atmosphere. Media was changed every 2–3 days. Discs were removed after incubation with cells for 2, 4, and 8 weeks for subsequent evaluation by electron microscopy and histological staining.

After 2, 4 and 8 weeks, the discs were removed and fixed in 2.5% glutaraldehyde. The specimens were post-fixed in 1% $OsO_4$ buffered with PBS for 1 hour at room temperature. The sample was washed in 3 changes of distilled $H_2O$, and dehydrated in an ethanol series (50%, 70%, 80%, 90%, and 100%). At this point ½ of the sample was processed for scanning electron microscopy (SEM) using a procedure described below. The sample for transmission electron microscopy (TEM) was infiltrated in a mixture of EPON-Araldite (EA) and 100% EtOH (1:1) overnight at room temperature. After 24 hours, the infiltration solution was replaced with EA, and infiltrated for an additional 48 hours. The samples were placed in flat molds, filled with resin, and the resin was polymerized at 60° C. for 48 hours. The EA resin blocks were cut with a DDK diamond knife, on a Reichert-Jung Ultracut E ultramicrotome. Thin (100 nm) sections were picked up on 200 mesh copper grids and stained with uranyl acetate and lead citrate. The sections were viewed on a Hitachi H-7100 TEM at 50 keV. Digital images (TIFF image format) were collected with an AMT Advantage 10 image acquisition system (AMT, Rowley, Mass.).

Dehydrated samples for SEM were critically point dried (CPD) using a Polaron E3000 CPD apparatus. The samples were dried from $CO_2$ at 38° C. and 1200 psi. Dried samples were mounted on aluminum specimen stubs, and coated with gold using a Pelco SC-2 Sputter Coater. The samples were viewed using a Hitachi H-2460N SEM at 5 keV. Images were digitally recorded (TIFF image format) using a PC-based Quartz PCI image management system (Quartz Imaging Corporation, Vancouver, Canada). SEM and TEM were used to examine cellular activity on the surface of the scaffolds as well as deep within the scaffolds.

Figure 3:
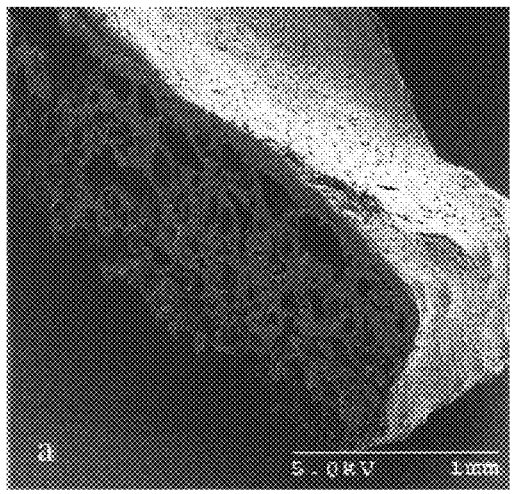
FIG. 3 illustrates scanning electron micrographs (SEM) of: (a) in vitro cultured bone marrow stromal cells at 4 weeks; (b) in vitro cultured bone marrow stromal cells at 8 weeks; (c) in vitro fresh bone marrow at 4 weeks; and (d) in vitro fresh bone marrow at 8 weeks.
Figure 3:
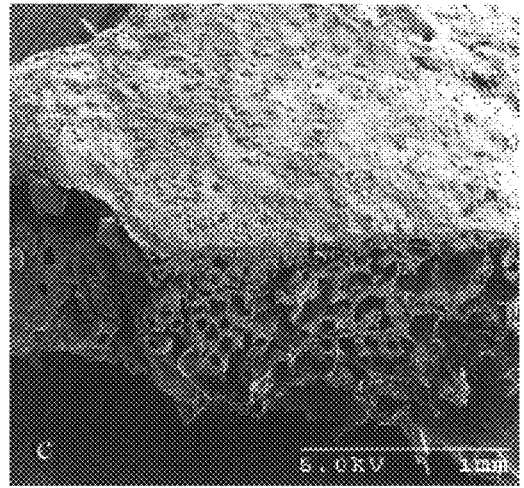
Figure 3:
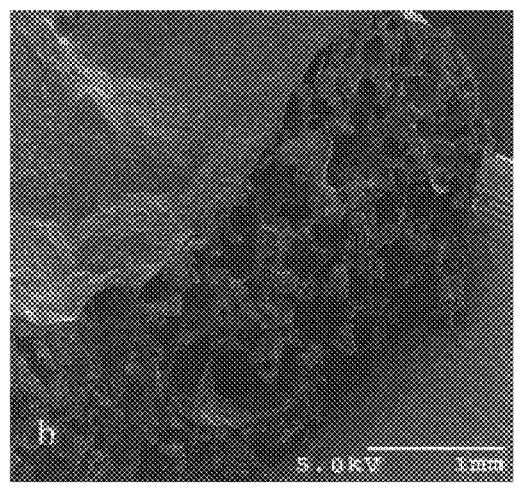
Figure 3:
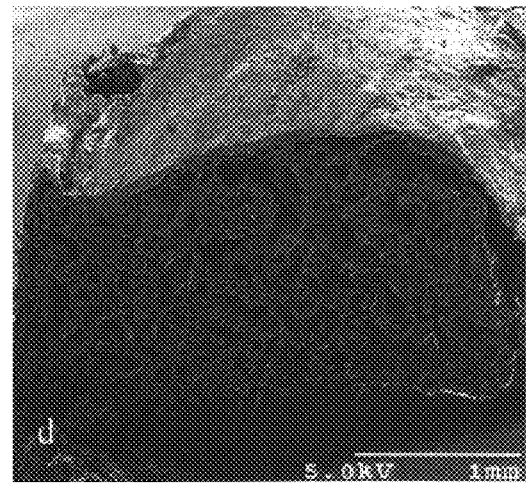

SEM displayed confluent cell layers on the surface of the seeded discs at each time point regardless of the cell source. FIG. 3 displays SEM micrographs of discs at 4 and 8 weeks seeded with cultured bone marrow stromal cells (FIGS. 3a and 3b) and fresh bone marrow (FIGS. 3c and 3d). Unseeded discs did not display any cellular activity (not shown). There is little differences in the surfaces as seen with SEM. Both the cultured bone marrow stromal cell samples and fresh bone marrow samples sustained thick confluent layers of cells on the surface as well as cellular activity within the scaffolds.

Figure 4:
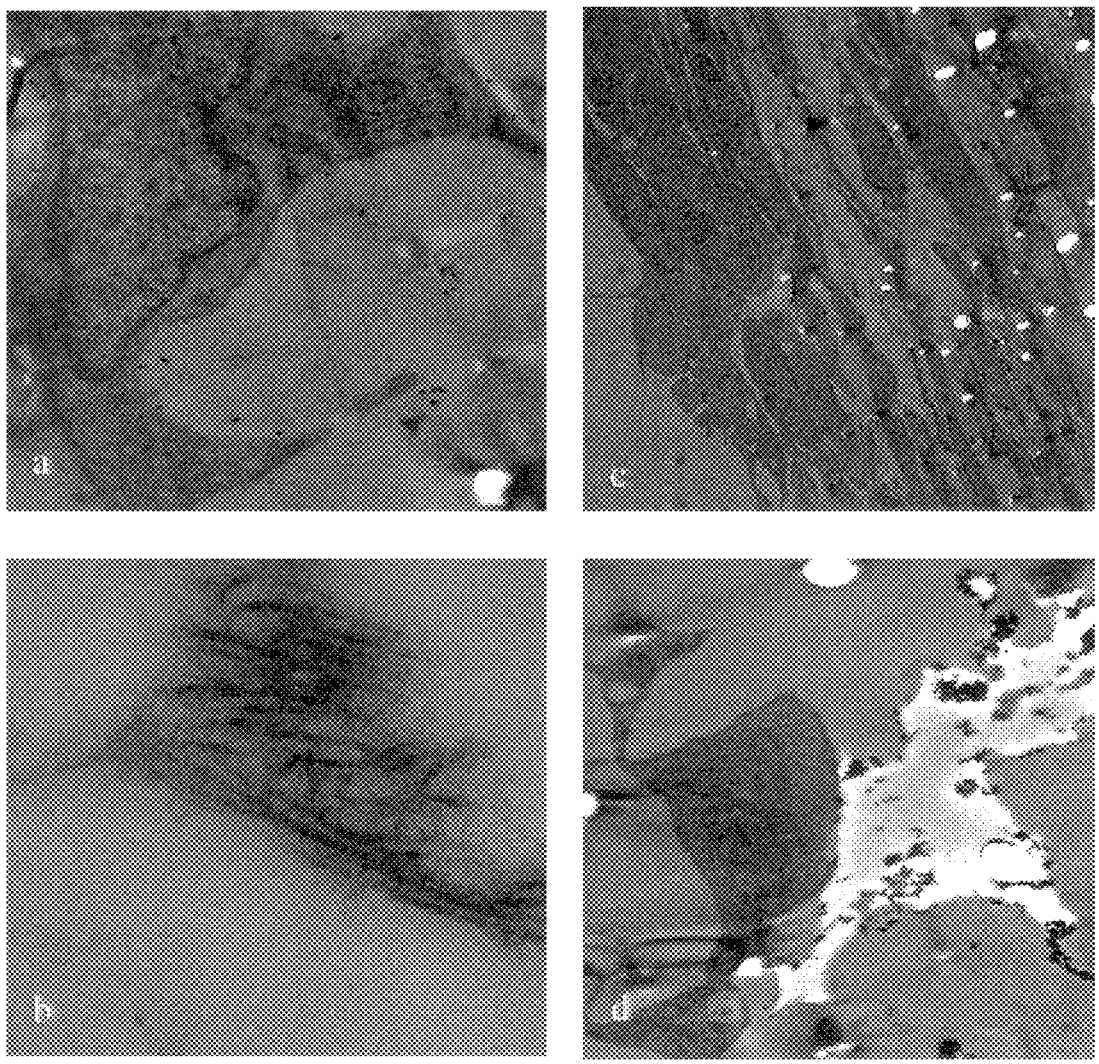
FIG. 4 illustrates a transmission electron micrographs (TEM) of in vitro: (a) cultured bone marrow stromal cells at 4 weeks at 40,000 times magnification in scaffold; (b) cultured bone marrow stromal cells at 8 weeks at 100,000 times magnification showing formulation of banded collagen; (c) fresh bone marrow at 2 weeks at a magnification of 6,000 times; (d) cell/polymer interface at 8 weeks at a magnification of 8,000 times.

FIG. 4 displays TEM micrographs of in vitro disks which are cultured bone marrow stromal cells at 40,000 times magnification. The cell FIG. 4(a) is deep in the scaffold. FIG. 4(b) shows the cultured bone marrow stromal cells at 8 weeks at 100,000 times magnification showing the formation of banded collagen. FIG. 4(c) shows fresh bone marrow at 2 weeks magnified 6,000 times at the cell layers at the surface. FIG. 4(d) illustrates the cell/polymer interface which is 300 microns into the scaffold at 8 weeks magnified 8,000 times. Each of the TEMs shown in FIG. 4, specifically 4(a), 4(b), 4(c) and 4(d), are based on in vitro methods.

Figure 7:
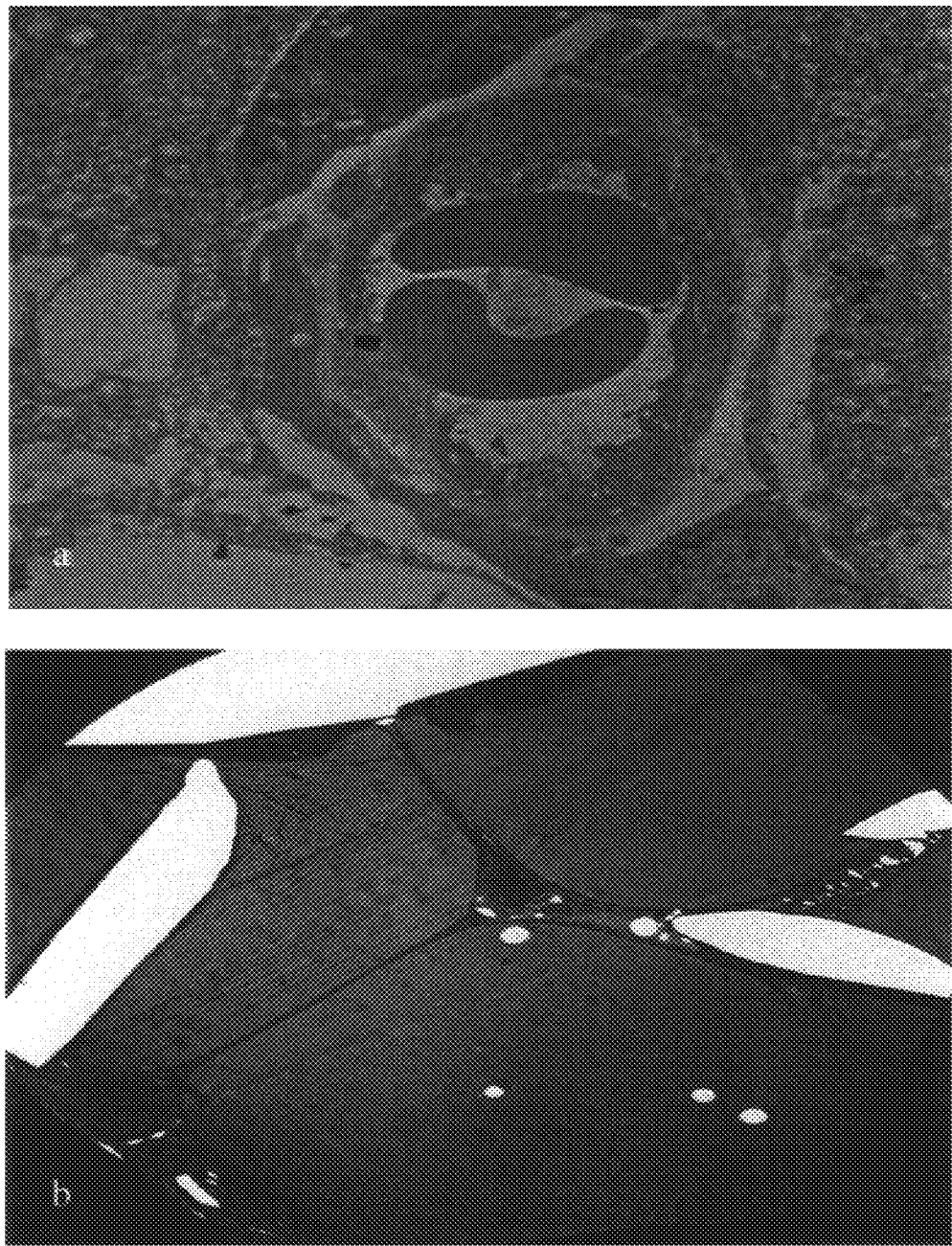
FIG. 7 illustrates a TEM of (a) the seeded implant of FIG. 6 at 8 weeks at 5,000 times magnification; (b) the unseeded scaffold at 8 weeks at 500 times magnification.
Figure 8:
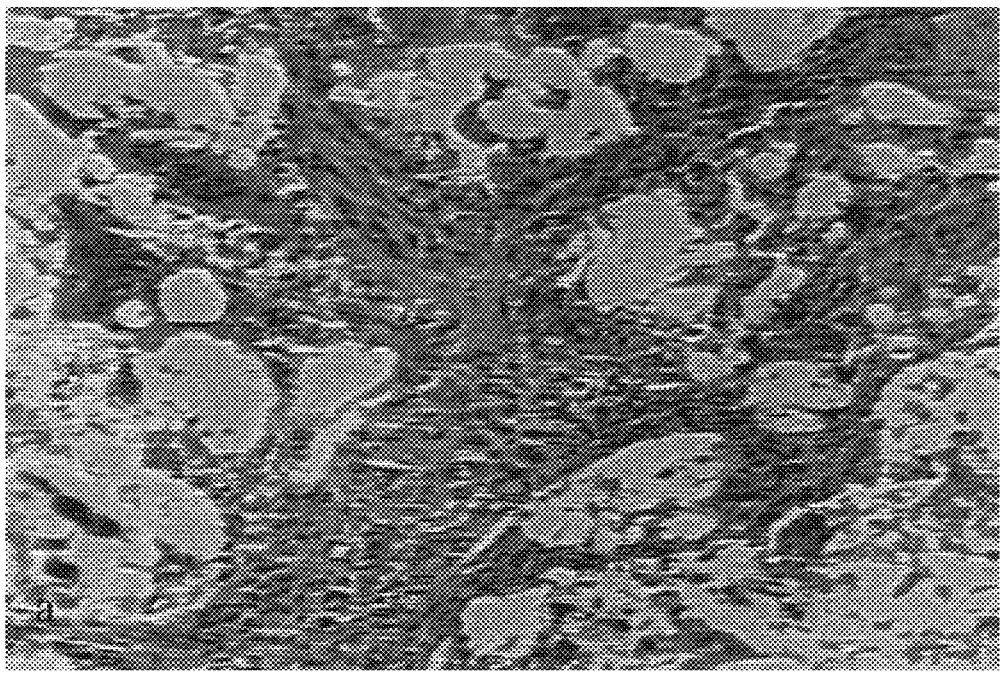
FIG. 8 illustrates in vivo (a) hematoxylin and eosin stain of the seeded implant and (b) illustrates unseeded implant at 8 weeks.
Figure 8:
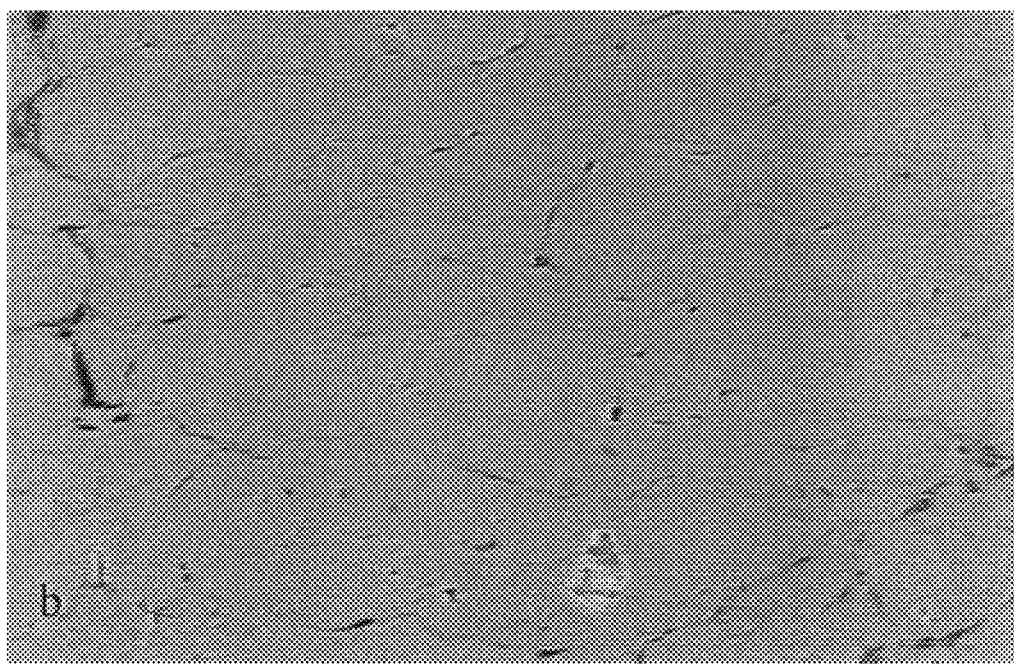

Both FIG. 3 and FIG. 4 display images that are abound with vital cells. The beginning of collagen formation is also seen. FIG. 7 displays TEM micrographs of the cultured bone marrow stromal cell samples after 8 weeks in culture. Analysis at 0.1 mm–0.5 mm deep into the scaffold displayed cellular activity, including live cells and collagen formation. Live cells and collagen production is seen throughout the scaffolds.

Slides of cross-sections of the discs were prepared and stained with Hematoxylin and Eosin (H & E) after 2, 4 and 8 weeks in culture. The samples were fixed in 2.5% glutaraldehyde. Standard dehydration in sequentially increasing alcohol solutions to 100% ethanol was performed, followed by immersion in xylene, next in paraffin-saturated xylene, and then in molten paraffin. Tissue blocks were sectioned at 5 microns, and stained by hematoxylin and eosin (H & E) as well as Masson's trichrome. Slides were prepared in quadruplicate of the cross-section in the center of the discs after 2, 4 and 8 weeks. Slides were imaged into a PC using a video capture program (VidCap 2.0), then transferred first into Adobe Photoshop 4.0 and then further into NIH Image 1.61 for analysis. The results are an average of 5 random fields on three different samples with two areas analyzed on each sample (total of 60 fields per analysis).

Figure 5:
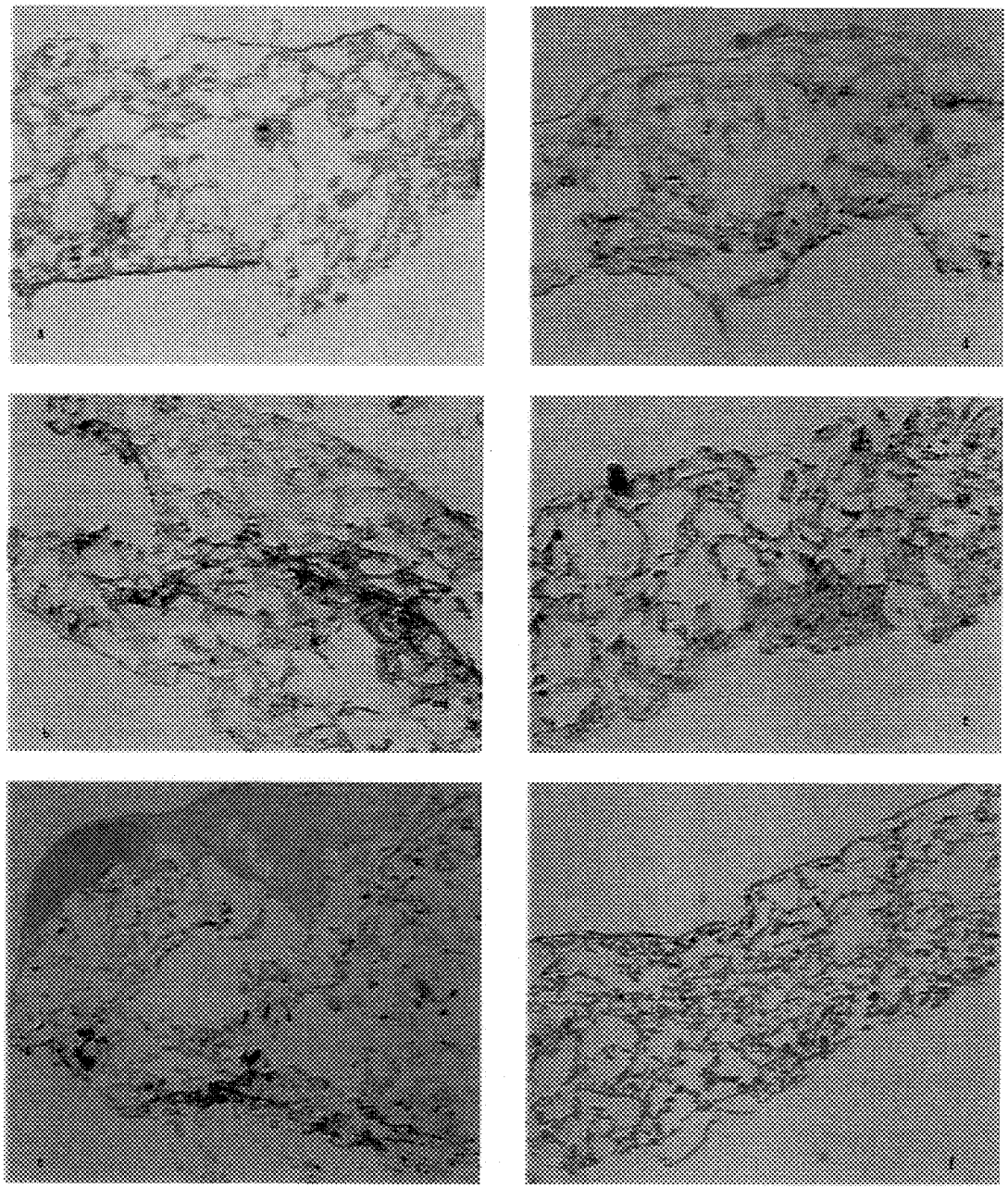
FIG. 5 illustrates in vitro hematoxylin and eosin (H&E) staining of cross-sections of cultured cells (a–c) at a) 2 weeks; b) 4 weeks; and c) 8 weeks and primary bone marrow stromal cells (d–f) seeded samples (fresh bone marrow) at d) 2 weeks; e) 4 weeks and f) 8 weeks.

The H&E staining of cross-sections of cultured cells (a through c) and primary bone marrow stromal cells (d through f), seeded samples (fresh bone marrow), are shown in FIG. 5. Micrograph (a) is shown at 2 weeks, (b) at 4 weeks and (c) at 8 weeks and (d) at 2 weeks, (e) at 4 weeks and (f) at 8 weeks in vitro. Live cells are evident throughout the scaffold with many cells on the surface. Mineralization is seen in the 8 week cultured samples, forming a "capsule" around the scaffold. This data is shown below in Table 2 wherein it is indicated there is no significant difference in the degree of tissue ingrowth for samples seeded with fresh bone marrow compared to samples seeded with cultured bone marrow stromal cells (T-test results: p>0.05 at each time point).

TABLE 2

In Vitro histomorphometry
(positive stain of H&E slides after incubation)

|  | Cultured Bone Marrow Stromal Cells (%) | Fresh Bone Marrow (%) |
|---|---|---|
| 2 weeks | 17.51 ± 2.43 | 17.36 ± 5.43 |
| 4 weeks | 26.14 ± 6.06 | 24.22 ± 3.66 |
| 8 weeks | 19.87 ± 3.84 | 21.27 ± 5.39 |

The combination of PCL, PLGA and HA results in a unique, shapeable material as a scaffold for bone tissue engineering. Electron microscopy (EM) results indicate cell growth throughout the scaffold, and this is confirmed by histological analyses. EM results demonstrate live cells throughout the scaffold beginning to produce collagen about 500 microns deep into the scaffold. Previously, cells were shown to migrate only 200–300 microns into scaffolds. PCL spherulites are also seen indicating a phase separation of PCL and PLGA. After 8 weeks incubation, there is a noticeably increased amount of collagen throughout the scaffolds.

Histomorphometric analysis also indicates seeding with fresh bone marrow is comparable to cultured bone marrow stromal cells (see Table 2). After 8 weeks incubation, the scaffolds contained approximately 20% cellular/tissue ingrowth. The amount of tissue ingrowth throughout the 10/90 blend+10% HA scaffold is similar with both the cultured cells and the fresh bone marrow. The porosity of the scaffold is evident in the Figures, indicating degradation. Both EM and histological results indicate that the simpler seeding of fresh bone marrow at the time of implantation is comparable to the timely two week culture of the bone marrow to obtain primary bone marrow stromal cells.

In vivo of the present invention confirms the applicability of the present invention as a tissue substitute, the contemplated use of the present invention. Scaffolds constructed of the composition of the present invention support the growth of bone both in vivo and in vitro. The in vivo data supports the use of a blend of the present invention comprising poly(lactic-co-glycolic) acid, polycaprolactone and particulate hydroxyapatite. The degradation time of PCL is typically slower than that of poly(lactic-co-glycolic) acid. The blends of the two polymers have advantageous controlled properties, such as mechanical strength and degradation time. Polycaprolactone is utilized because it is crystalline and demonstrates high solubility, blend miscibility (when in small concentrations), nontoxicity, and biodegradability. PLGA is chosen for its amorphous nature, biodegradability, and nontoxicity.

The in vitro cell, two-dimensional studies of rabbit bone marrow stromal cells onto spun-cast films of the polymers confirmed the osteoconductive potential of the polymer blends. Results indicate that polycaprolactone is a better substrate for the growth of cells, whereas PLGA is a preferred substrate for the ossification of the attached bone cells. Additionally, the blends appear to be superior to the homopolymers for inducing both bone growth and ossification.

In the in vivo testing, nine six-month old, male New Zealand White Rabbits (*Orycytolagus cuniculis*) were purchased from a rabbit supplier (Myrtle's Rabbitry, Inc., Thompson Station, Tenn., 37179). All rabbits were housed individually and had ad-libitum access to Purina Rabbit Chow and water. All rabbits were followed for 4–12 weeks postoperatively.

All animals were anesthetized with an intramuscular (IM) injection (0.59 mL/kg) of a solution of 91% ketamine hydrochloride (Ketaject, 100 mg/mL, Aveco, Fort Dodge, Iowa) and 9% xylazine (Xylaject, 20 mg/ml, Mobay Corp, Shawnee, Kans.). The rabbit was positioned in the supine position and the lower abdominal wall, inguinal region, and lateral surfaces of both thighs and legs were shaved, dipilitated, and prepared for aseptic surgery. A 4 cm long skin incision was made on the anterior aspect of the patella, and the quadriceps femoris muscle tendon was displaced laterally. A drill and cutting burr was used to create a small femoral and tibial defect and a Fogarty balloon catheter was used to harvest bone marrow from the medullary canal. The bone marrow plugs were harvested by inflating the balloon and withdrawing it from the canal.

The bone marrow plugs were then mixed with 4 mL of heparinized IMDM tissue culture medium (GIBCO Laboratories, NY) in a test tube. The marrow was disaggregated by passing it gently through an 18 gauge IV catheter and syringe to create a single cell suspension. The suspension was then centrifuged (250 g, 10 minutes) and some of the supernatant was discarded to concentrate the cell number. Two milliliters of venous blood was taken from the femoral vein through a small incision and autogenous serum was obtained by centrifugation. After adding autogenous serum (10% of total volume), the viability of the cells was >90% as checked by the tryptan blue dye exclusion method, and the number of nucleated cells were controlled to more than $1 \times 10^8$/mL. Polymer/ceramic composite scaffolds were then soaked in this cell suspension by placing them individually into a 24 well plate.

A 12 cm longitudinal incision was then made in the midline of the lower abdominal region of the rabbit. The right and left deep inferior epigastric arteries and veins within the rectus abdominis muscles are dissected out and identified. This is done under loupe magnification. The scaffolds of the present invention were placed intramuscularly, adjacent and superficial to the deep inferior epigastric vascular bundle. The seeded scaffolds were placed on the right vascular bundle, and the unseeded scaffolds were placed on the left side to serve as untreated controls. Incisions were closed with 4-0 vicryl suture. All rabbits then received an IM injection (2.5 mg/kg) of an antibiotic (Baytril, Bayer Corp., Shawnee Mission, Kans., 66201) pre- and postoperatively for 1 day as a prophylaxis for infection. Postoperative pain control was managed with Rompun.

At 4, 8 and 12 weeks postoperatively, three rabbits were anesthetized with an IM injection of ketamine and xylazine and the abdominal aorta and inferior vena cava were exposed through a laparotomy incision. Lactated Ringer's solution, warmed to 37° C., with 1% lidocaine was infused through a 21 gauge angiocatheter placed in the aorta. The vena cava was vented to prevent overfilling. During this infusion, the animal was euthanized with an overdose (45 mg/kg) of pentobarbital (Nembutal, Abbott Laboratory, Chicago, Ill.). Blood was replaced with a radiopaque silicon agent (Microfil) which was infused manually through the same catheter. The scaffolds were dissected free from the surrounding soft tissue and a radiograph of the abdominal region, scaffold, and perfused blood vessels were obtained using a Phillips Oralix 70 dental x-ray unit at an exposure of 50 kV, 7 mA, and 0.25 seconds, and a tube-to-cassette distance of 152 cm. The NIH Guide for the Care and Use of Laboratory Animals was utilized and experiments were conducted under the control of an Animal Care and Use Committee (IACUC). Results indicate that the polymer/ceramic scaffold is indeed a good substrate for bone cell growth.

The present invention, for example, in one millimeter thick sheets, may be used for facial skeletal reconstruction, specifically, orbital floor reconstruction, alveolar ridge augmentation, and nasal reconstruction. Thicker versions of the material may be laminated to create stronger, bulkier bone substitutes for other applications. These include cranioplasty, genioplasty and chin augmentation, palate reconstruction, and other large bony reconstructions. Other potential applications for this material include the treatment of bony non-unions, spinal fusion, and replacement of long bone defects, fixation devices, etc. Because of its ability to become completely replaced by bone, it is possible that this material will be a viable substitute for any application where traditional bone grafts have been used (autograft and allograft).

Figure 6:
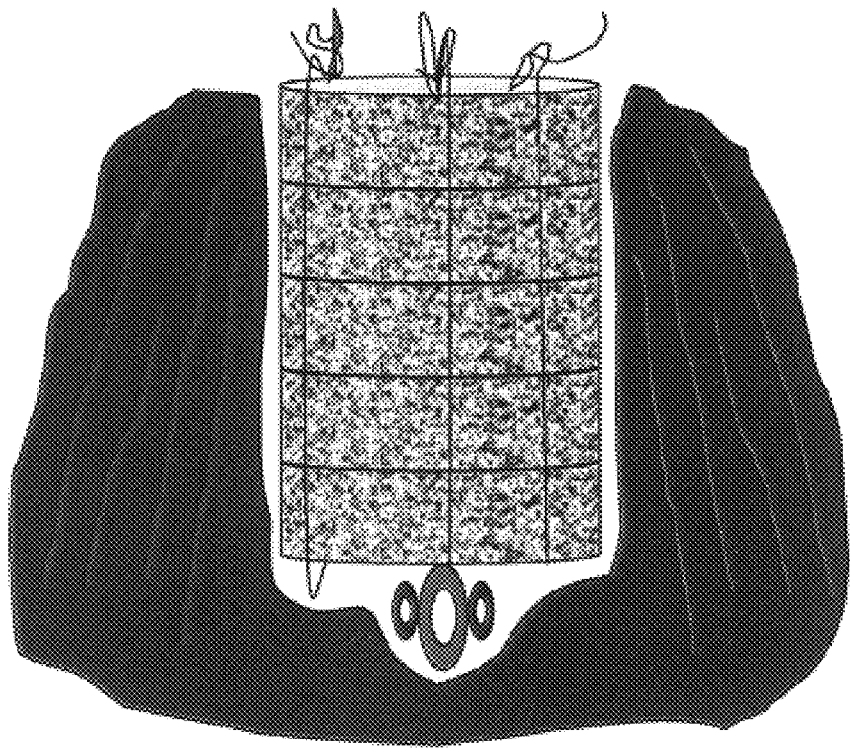
FIG. 6 illustrates a schematic representation and a SEM of an in vivo implant according to the present invention.
Figure 6:
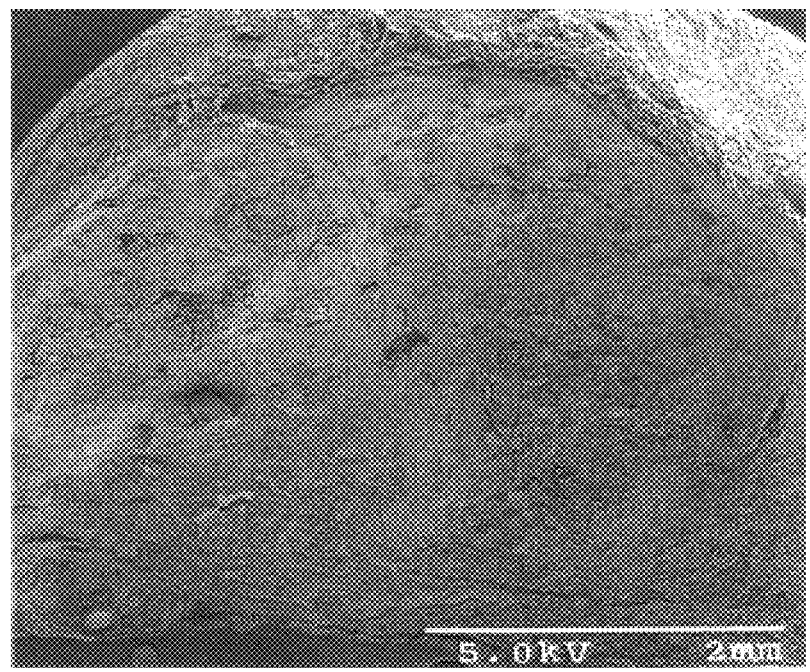

FIG. 6 illustrates the present invention which has been implanted in vivo. FIG. 6(a) illustrates a schematic an implant which is seeded with the present invention. FIG. 6(b) illustrates a SEM of an implant seeded with the present invention. It is preferable that the seeded implant of the present invention have greater tissue ingrowth and increased vascularization and increased bone formation. At 8 weeks, seeded implants in accordance with the present invention had approximately 34% tissue ingrowth as compared to 19% tissue ingrowth in unseeded examples. There was also vascularization and primitive bone formation in the seeded sample while there was little or none of either in the unseeded samples. This was confirmed by fluorochrome staining, TEM, and Masson's Trichrome staining.

FIG. 7(a) illustrates a transmission electron micrograph of the in vivo seeded implant at 8 weeks showing the blood vessels formed within the scaffold at 5,000 times magnification. FIG. 7(b) shows an unseeded scaffold at 8 weeks at 500 times magnification which is porous.

Commercial HA (Aldrich Chemical Co.) and chemically synthesized HA are appropriate sources of hydroxyapatite utilized in the synthesis of the composites. Addition of HA tends to increase osteoconductivity, but in too high a concentrate decreases mechanical strength. Various approaches may be made to alter the size and morphology of the HA material. The approaches are based on rapid and delayed precipitation in an aqueous environment. Controlling the particle (varying from nanocrystalline to submicron and micron domains (~10 nm–10 $\mu$m)), and the morphology of the HA particles appears to impact the properties of the biocompatible materials. One approach involves reacting a solution of $Ca(OH)_2$ and $H_3PO_4$. Another approach involves a delayed precipitation reaction involving a solution of $Ca(NO_3)_2$ and $(NH_4)_2HPO_4$. A modified sol-gel process comprises dissolving $P_2O_5$ in anhydrous alcohol such as ethanol or ethylene glycol to generate a partially hydrolyzed P-alkoxide. Calcium is introduced into this solution either as a metal or as a salt such as the acetate. Calcium metal is known to react with alcohol to generate the alkoxide. In the present case, the alkoxide solution is formed first followed by addition of the alcoholic solution containing $P_2O_5$. The resulting clear solution is then hydrolyzed at a pH of 6–8 to induce the formation of HA. The precipitates formed are collected either by rotary evaporation or centrifugation. The powders collected are dried and heat-treated to crystallize and grow the HA crystallites. A complete gelation reaction was also tried in order to synthesize a 3D interconnected gel structure. The gels are dried under ambient conditions to generate xerogels. The desirability of the above sol-gel process is the ability to synthesize P-alkoxide in-situ and also control the reaction between Ca and P to yield fine particles with different morphologies and sizes.

For example, although hydroxyapatite is osteoinductive and osteoconductive, osteogenic properties of hydroxyapatite are, however, a strong function of the composition as well as the microstructure of the hydroxyapatite particles. For example, synthesis of porous hydroxyapatite containing interconnected channels of nanocrystalline hydroxyapatite grains could have a strong influence on stimulating cell response and growth. Additionally, control of the particle size and morphology may also have a strong influence on the resorbable characteristics of hydroxyapatite which are driven by surface activity. Thus, synthesis and generation of finely oriented hydroxyapatite particles may have a tremendous impact on the cellular activity and biodegradable response of the biocompatable materials Many major bony defects or abnormalities (i.e. congenital defects of the cranio-facial skeleton) exist which would be benefited by the present invention. Many children undergo multiple operations throughout their lives requiring bone grafts taken from ribs, iliac crest, and local calvarial bone. One millimeter thick sheets of the present invention may be used for facial skeletal reconstruction, specifically, orbital floor reconstruction, alveolar ridge augmentation, and nasal reconstruction. Thicker versions of the material may be utilized to create stronger, bulkier bone substitutes for other applications. These include cranioplasty, genioplasty and chin augmentation, palate reconstruction, and other large bony reconstructions. Other applications for the material of the present invention include the treatment of bony non-unions, spinal fusion, and replacement of long bone defects. Because of its ability to become completely replaced by bone, this material is a viable substitute for any application where traditional bone grafts have been used. Additionally, this material may be used to coat existing prosthetic materials or prostheses to allow for better bony integration. Another application of this material is for the creation of a bone plating system for the repair of fractures and for the fusion of joints. This material is capable of being shaped into plates similar to commercially available metallic plates. Screws can also be milled from this material. However, in the case of screw, reduced or even no amounts hydroxyapatite should be used because hydroxyapatite renders the end product more brittle. Similarly if the material is used to augment or substitute breast tissue, little or no hydroxyapatite should be used because calcification or mineralization is not desirable in this tissue.

Articles such as medical devices may be molded from the composites of the present invention by use of various conventional injection and extrusion processes and molding equipment equipped with dry nitrogen atmospheric chamber (s) at temperatures ranging from about 110° C. to about 230° C., more preferably about 120° C. to about 220° C., with residence times of about 1 to about 10 minutes, more preferably about 2 to about 5 minutes.

The composition of this invention can be melt processed by numerous conventional methods to prepare a vast array of useful devices. The materials of the present invention can be injection or compression molded to make implantable medical and surgical devices, especially bone regenerating substitutes. The preferred devices include preformed bone defect substitutes, bone waxes, and cartilage replacements.

Additionally, the composition of the present invention can be administered to the site by means of conventional delivery devices. The device can be a conventional syringe, with or without mechanical assistance, a caulking-like gun, a soft-sided tube, etc., and the like. Alternatively, the composition can be extruded to prepare fibers. The filaments thus produced may be spun as multifilament yarn, or meshes, knitted or woven, and formed by conventional molding techniques into reinforced devices and utilized where it is desirable that the structure have high tensile strength and desirable levels of compliance and/or ductility. Useful embodiments include preformed defect bone substitutes, and cartilage replacements for areas where bone or cartilage tissues are damaged or surgically removed.

The composition of the present invention may also be used to coat substrates, such as biocompatible substrates such as meshes, medical devices, etc. The coatings would be made by utilizing liquid composition of the present invention which would then be applied to the substrate by conventional coating techniques such as dipping, spraying, brushing, roller coating, etc.

Additionally, the composition can be molded to form films which are particularly useful for those applications where a drug delivery matrix in hard tissues (e.g., growth factors) is desired. Furthermore, the composition of the present invention can be formed into foams, with open or closed cells, which are useful for applications where a high rate of hard tissue ingrowth is required such as in hard tissue replacement areas like the cheek, chin, and vertebrae.

The present invention may also be used as carrier or delivery vehicle for therapeutic agents (preferably a blend of a copolymer of poly(lactic) acid and poly(glycolic) acid and a polyester (e.g., polycaprolactone with or without hydroxyapatite).

The present invention is capable of binding proteins as well as supporting cell proliferation and differentiation. As a drug delivery system, protein-based pharmaceuticals may be bound to the composition with reliable binding and delivery of drug. It is expected that these biologics can be delivered at rates that are controllable and capable of manipulation such that the dosage and rate of delivery of the drug may be controlled based on the nature of the material and the nature of the binding interaction with the pharmaceutical. The pharmaceuticals that may be best served by this type of material include growth factors, peptide-hormones, and other peptide-based materials. Furthermore, lipid-encapsulated pharmaceuticals may also be delivered with this material. In this regard the present invention is suited for chemotherapeutic agents and other medications that would be best delivered as an implant. The advantage of this system over traditional intravenous delivery include: a single procedure to implant the drug-seeded material into a sub-cutaneous or locally effective area; uniform, controlled delivery of the pharmaceutical; drug delivered while bound to local and physiologically normal proteins; no need to remove the delivery system; and local delivery of drug may be directed with an implant so that systemic levels of the medication will not be necessary.

The present invention may also be useful as a cell delivery system. Since the material is capable of supporting the cells until they derive vascularization from the surrounding tissue, cells may be seeded into the material and then implanted into the host. The cells may be autogenous in nature, or they may be allogenic. The composition may or may not be modified with growth factors, or other pharmaceuticals to enhance engraftment/host acceptance. This aspect of the present invention has applications in a number of cell delivery systems. For example, bone marrow transplantation where the bone marrow cells are seeded into a porous form of the blend and then implanted subcutaneously or at some highly vascularized bed, such as the perinephric fat. In addition, pancreatic islet cells may be seeded into a porous form or precultured onto single layer sheets, layered into three-dimensional constructs and then implanted into the host into a highly vascularized bed of tissue as a way of delivering insulin producing cells for the treatment of diabetes mellitus. Hepatocytes may be culture expanded and seeded onto the material for a functional liver replacement. A more porous, spongiform embodiment may be used to create a delivery system for adipocytes and create a vascularized fat implant for the filling of tissue defects that are congenitally present or a result of trauma, breast reconstruction or augmentation, or other cosmetic augmentation procedures. Delivery of genetically altered cells, i.e. those cells transfected with a gene, that results in a population of cells that produces a gene product or series of products is also contemplated. This may be used for diseases where a genetic deficiency occurs, e.g. Gaucher's disease, or one where a genetic product may be therapeutic, e.g. local delivery of PDGF for healing of diabetic foot ulcers.

The compositions utilized in this invention may be administered by any number of routes, including but not limited to, intravenous, intramuscular, intra-arterial, intramedullary, intrathecal, intraventricular, transdermal, subcutaneous, intraperitoneal, intranasal, enteral, topical, sublingual, or rectal means. In addition to the active ingredients, the compositions may contain suitable pharmaceutically-acceptable carriers comprising excipients and auxiliaries which facilitate processing of the active compounds into preparations which can be used pharmaceutically. As used herein, the term "pharmaceutically acceptable carrier" refers to a carrier medium which does not interfere with the effectiveness of the biological activity of the active ingredients and which is not toxic to the hosts to which it is administered.

As used herein, the term "pharmacologically effective amounts" refers to the amount of the referenced component which results in an increase survival of the host, or results in a desirable clinical outcome. The "therapeutic index" is defined for purposes herein in terms of efficacy (e.g., extent of tumor or infection reduction or other cure) and/or in terms of toxicity to the host. For non-human hosts, if the efficacy increases at least 50% over the efficacy using an excipient control (e.g., phosphate buffered saline) and the ratio of mean body weight at the end of the evaluation period for efficacy response to mean body weight at the start of treatment is at least 0.90 (i.e., no greater than 10% body weight loss), the therapeutic index has increased. The ratio of mean body weights indicates the extent of toxicity, with a value of 1 indicating no toxicity. For non-human hosts begin treated for cancer, the extent of efficacy achieved may be measured by the ratio of mean tumor volume at the end of the evaluation period to mean tumor volume at the start of treatment. A reduction in the ratio of at least 50% of treated over excipient control indicates increased efficacy. The most preferred doses, schedules, and types of therapeutic agents are those that achieve a mean tumor volume ratio of between 0 and 5, with a value of 0 being optimum and indicating a cure. For human hosts, if the efficacy increases at least 50% upon treatment with the therapeutic agents and the toxicity is acceptable (i.e., no more than fever, chills, and/or general malaise) the therapeutic index has increased. For human hosts being treated for cancer, the extent of efficacy is generally ascertained in the clinic by measuring the perpendicular diameters of the products of all measured disease. The effect of the doses may diminish with time. For humans the dose may be repeated for months or even years.

A "therapeutically effective dose" refers to that amount of active ingredient which ameliorates the symptoms or condition. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population).

The term "cancer" as used herein refers to any neoplastic disorder, including such cellular disorders for example, renal cell cancer, Kaposi's sarcoma, chronic leukemia, breast cancer, sarcoma, ovarian carcinoma, rectal cancer, prostate cancer, throat cancer, melanoma, colon cancer, bladder cancer, mastocytoma, lung cancer and gastrointestinal or stomach cancer. Preferably, the cancer is colon cancer, breast cancer and gasteric cancer, melanoma, renal cell cancer, sarcoma, lung cancer, adenocarcinoma, prostate or breast cancer. Even more preferably the cancer is breast cancer.

The surgical and medical uses of the filaments, films, foams, molded articles, and injectable devices of the present invention include, but are not necessarily limited to osteoinductive and/or osteoconductive: orthopedic pins, clamps, suture anchors, sutures, surgical tacks, clips, plates and seal, screws, and plates; clips; staples; hooks, buttons, and snaps; performed bone substitutes; injectable bone cements; vertebrae disc; suture anchors; injectable defect fillers; performed defect fillers; bone waxes; cartilage replacements; spinal fixation devices; drug delivery devices; and foams, with open or closed cells, and others.

The composition of the present invention, when seeded with rabbit bone marrow stromal cells or fresh bone marrow, induce new bone formation. While not wishing to be bound by theory, it appears that the addition of poly(caprolactone) modifies the degradation times, increases the osteoconductivity potential, and enhances the mechanical properties of the composites of the present invention. 2D cell studies of the present invention have suggested that PCL is superior to PLGA for bone cell growth. The strengths and degradation rates can be optimized by adjusting the elements and molecular weights of the polymers such that the degradation rates are complementary to the new bone formation rate. The composition of the present invention has the potential to obtain mechanical strengths that are comparable to trabecular bone. The material is easily cut, molded and shaped. The combination of the osteoconductive polymers with osteoinductive hydroxyapatite results in a superior substrate for bone cell growth. The present invention's PLGA/PCL/HA composites, are osteoconductive, osteoinductive, shapeable and mechanically strong. Thus, synthetic, resorbable tissue grafts formed from this material are possible.

While the foregoing has been set forth in considerable detail, the embodiments, procedures and compositions are presented for elucidation, and not limitation. Modifications and improvements, including equivalents, of the technology disclosed above which are within the purview and abilities of those in the art are included within the scope of the claims appended hereto. It will be readily apparent to those skilled in the art that numerous modifications, alterations and changes can be made with respect to the specifics of the above description without departing from the inventive concept described herein.

What is claimed is:

1. A composition comprised of:
   a bioceramic material;
   a polycaprolactone; and
   a copolymer of poly(lactic) acid and poly(glycolic) acid;
   said copolymer and said polycaprolactone blended at a predetermined ratio, said predetermined ratio being in the range of from about 10:90 polycaprolactone to copolymer to about 50:50 polycaprolactone to copolymer.

2. The composition of claim 1 wherein said composition is suitable as a bone substitute.

3. The composition of claim 1, further comprising a therapeutic agent.

4. The composition of claim 1 wherein said bioceramic material is a hydroxyapatite.

5. A method of treating a patient for a boney defect comprising the steps of:
   mixing a polycaprolactone and a copolymer of poly(lactic) acid and poly(glycolic)acid to form a blend having a ratio of polycaprolactone:copolymer in the range of about 10:90 to about 50:50;

adding a bioceramic material to said blend;

molding said blend and said bioceramic into an implant; and implanting said implant into said patient.

6. The method of claim 5, wherein said implant is selected from the group consisting of a bone prosthesis, a hard tissue implant, and a bone scaffold.

7. The method of claim 5, wherein said bioceramic is hydroxyapatite.

8. The composition of claim 1, wherein said copolymer is at a ratio of about 65:35 lactic acid:glycolic acid.

9. The method of claim 5, wherein said implant is osteoconductive.

10. A method of treating a patient for a cranio-facial defect comprising the steps of:

mixing a polycaprolactone and a copolymer of poly (lactic) acid and poly(glycolic)acid to form a blend having a ratio of polycaprolactone:copolymer in the range of about 10:90 to about 50:50;

adding a bioceramic material to said blend;

molding said blend and said bioceramic into an implant; and implanting said implant into said patient.

11. A method of treating a patient in need of a bone substitute comprising the steps of:

mixing a polycaprolactone and a copolymer of poly (lactic) acid and poly(glycolic)acid to form a blend having a ratio of polycaprolactone:copolymer in the range of about 10:90 to about 50:50;

adding a bioceramic material to said blend;

molding said blend and said bioceramic into an implant; and implanting said implant into said patient.

12. The method of claim 5, wherein said implant is a prosthetic template.

13. The method of claim 5, wherein said implant is a template for bone formation.

14. The method of claim 5, wherein said copolymer is at a ratio of about 65:35 lactic acid:glycolic acid.

15. The method of claim 10, wherein said copolymer is at a ratio of about 65:35 lactic acid:glycolic acid.

16. The method of claim 11, wherein said copolymer is at a ratio of about 65:35 lactic acid:glycolic acid.

* * * * *